United States Patent [19]

Stanley et al.

[11] Patent Number: 4,908,110

[45] Date of Patent: Mar. 13, 1990

[54] LASER-INDUCED NITRATION

[75] Inventors: Ann E. Stanley; Susan E. Godbey, both of Huntsville, Ala.

[73] Assignee: The United States of America as represented by the Secretary of the Army, Washington, D.C.

[21] Appl. No.: 340,815

[22] Filed: Apr. 17, 1989

[51] Int. Cl.[4] .................................................. B01J 19/08
[52] U.S. Cl. .............................. 204/157.61; 568/947; 204/157.81; 204/157.82
[58] Field of Search ........................ 568/943, 947, 948; 260/688; 204/157.61, 157.81, 157.82

[56] References Cited

U.S. PATENT DOCUMENTS 3,780,115 12/1973 L'honore et al.

OTHER PUBLICATIONS

G. B. Bachman, L. M. Addison, J. V. Hewlett, L. Kohn, and A. Millikens, "Nitration Studies. I. General Mechanism of Vapor Phase Nitration", J. Org. Chem. 17, 906 (1952).

R. E. Kirk and D. F. Othmer, "Encyclopedia of Chemical Technology," 2nd Edition, V13, New York, Wiley, "Nitration", pp. 784–796, (1967).

M. E. Umstead, J. W. Fleming, and M. C. Lin, "Photonitration of Hydrocarbons with Lasers", IEEE J. of Quantum Elect. 16(11), 1227 (1980).

F. E. Blacet, T. C. Hall, and P. A. Leighton "The Photochemistry of Nitrogen Dioxide at 3130 and 4050 Å", J. Am. Chem, Soc, 84, 4011.

M. E. Umstead, S. A. Doyde, J. W. Fleming and M. C. Lin, "Laser-Induced Reaction of $NO_2$ in the Visible Region", Appl. Phys. B38, 219 (1985).

Primary Examiner—John F. Terapane
Assistant Examiner—Susan Wolffe
Attorney, Agent, or Firm—Freddie M. Bush; James T. Deaton

[57] ABSTRACT

Infrared laser-induced production of nitrated products is achieved by irradiating compounds selected from propane, n-butane, isobutane, n-pentane, and cyclopropane in the gas phase while in a stainless steel cell $5 \times 5 \times 10$ cm equipped with zinc selenide windows to admit the infrared laser radiation in the range of 10.4 or 9.4 micrometers provided by a continuous wave $CO_2$ laser. KCl windows on the short path are to monitor infrared spectra of reactants and products. Nitrogen dioxide or nitric acid is present as the second reactant and the nitrating agent. The infrared laser-induced method far exceeds the yield of nitrated products found in the argon-ion laser-induced nitration of isobutane reported in the literature. Applicants' method at least equals the yield from thermally activated systems with a minimum formation of undesirable side products. A representative sample, 220 torr of gaseous butane and 20 torr $NO_2$ is irradiated in one experiment for 30 seconds with 75 W/cm$^2$ at a frequency of 956 cm$^{-1}$. About 40% of the $NO^2$ is converted to nitrocompounds. Identified as nitro-products are nitromethane, nitroethane, 1-nitropropane, 1-nitrobutane and 2-nitrobutane. More than 60% of the nitro-products are in the long chain forms, 1-nitrobutane and 2-nitrobutane. Pressure of the $NO_2$ reactant range from about 20 to 30 torr while the hydrocarbon reactant pressure range from about 200 to about 500 torr. Irradiation times ranges from about 30 to about 60 seconds. Laser powers range from 75 watts/cm$^2$ to about 82 watts/cm$^2$.

5 Claims, 4 Drawing Sheets

LASER-INDUCED NITRATION

DEDICATORY CLAUSE

The invention described herein may be manufactured, used, and licensed by or for the Government for governmental purposes without the payment to us of any royalties thereon.

BACKGROUND OF THE INVENTION

Most of the nitrated compounds used by the Army are in the form of explosives and propellants. Current nitration methods often result in low yields of desired products and complex mixtures of reaction products from side reactions. Complex mixtures of reaction products in propellants can produce undesired results.

Traditionally, nitration of paraffins in the thermally-induced methods is difficult to accomplish. High temperature (200°–400° C.) and high pressure (8–12 atmospheres) reactors are used with some success in the commercial production of nitroalkanes. However, new methods are continually sought which will increase the currently low yields of nitroparaffins and minimize the troublesome side reactions. Efficient control over which nitroalkanes are produced (selective nitration) in these processes is also desirable.

Recently, Umstead, et al. J. Quant Elect. QE-16, 1227 (1980), reported the photonitration of isobutane by nitrogen dioxide ($NO_2$) using an argon-ion laser as the excitation source. The $NO_2$ absorbs the radiation and then according to the kinetic modeling Unstead et al, Applied Physic B38, 219 1985) the vibronically excited $NO_2$ ($NO_2^{*+}$) achieves the direct abstraction of a hydrogen atom from the isobutane. The resulting free radical reacts primarily with $NO_2$ to form 2-methyl-2-nitropropane. However, the yield of 2-methyl-2-nitropropane based on isobutane was low (about 2.6%) and product fragmentation was reported to be significant.

The thermally-induced reaction between alkanes and $NO_2$ is described as proceeding via a free radical mechanism. The primary reaction steps are thought to be:

$$RH + NO_2 \rightarrow R\cdot HNO_2 \rightarrow R\cdot + \cdot OH + NO \quad (1)$$

and $$R\cdot + \cdot NO_2 \rightarrow RNO_2. \quad (2)$$

In the thermally-induced nitration of hydrocarbons, RH, using $NO_2$, an important side reaction is $$R\cdot + \cdot ONO \rightarrow RONO \quad (3)$$

in which an unstable alkylnitrite, RONO, is formed. The alkylnitrite decomposes as follows:

$$RONO \rightarrow RO\cdot + NO \quad (4)$$

although at conditions usually employed for nitrating hydrocarbons with $NO_2$, some of the alkylnitrite might not decompose. The alkoxy radical, RO, produced in reaction (4), may undergo any of a number of reactions, including the following, using propyl radicals as examples:

$$CH_3CH_2CH_2O \longrightarrow CH_3CH_2 + CH_2O \quad (5)$$

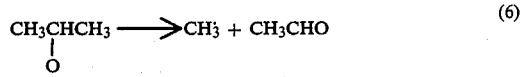

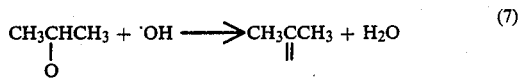

$$RO\cdot + RH \longrightarrow ROH + R\cdot \quad (8)$$

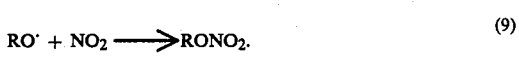

$$RO\cdot + NO_2 \longrightarrow RONO_2. \quad (9)$$

The continued oxidation of aldehydes, ketones, alcohols, etc. produces acids, oxides of carbons, water, etc. The alkyl radicals formed in reactions (5), (6), and (8) could react with $NO_2$ to form lower molecular weight nitroalkanes. Alkyl radicals can also decompose directly to form lower molecular weight alkyl radicals which could react with $NO_2$ to form shorter chain nitroalkanes.

A method to achieve nitration of hydrocarbons which produces less undesirable compounds in side reactions as illustrated by the above equations for thermally-induced reaction is highly desirable, particularly to meet both explosive and propellant requirements of the Army.

Therefore, an object of this invention is to provide a method for laser-induced nitrations of hydrocarbons wherein the nitration reactions are driven toward specific end products required for propellants with the chemical composition necessary to burn exactly with high energy production while having a minimum of side products which create undesirable smoke.

Another object of the invention is to provide a method for laser-induced nitrations of hydrocarbons to selectively nitrate these hydrocarbons to secondary nitrohydrocarbons having the same chain length as the reacting hydrocarbon.

SUMMARY OF THE INVENTION

A tunable infrared laser is used to induce the reaction of nitrogen dioxide with hydrocarbons of 3, 4 and 5 carbon atoms. Specifically, the tunable continuous wave (CW) infrared laser is used to drive the reaction between nitrogen dioxide, $NO_2$, and propane, n-butane, and n-pentane. The major products of the reactions are secondary nitrohydrocarbons, of the same chain length as the reacting hydrocarbon. Some short chain-nitrated compounds are also identified. The yield of 2-nitrobutane observed in the nitration of butane is ~20% based on the depletion of $NO_2$. The propane reacted with $NO_2$ to produce mostly 2-nitropropane with a smaller yield of ~5-9%. The analogous reaction of pentane yielded ~9% of the major product which is believed to be 2-nitropentane.

A stainless steel cell of exterior dimensions 5×5×10 cm is used to hold reactants during irradiation times from about 30 to about 60 seconds. This cell is equipped with zinc selenide windows on the long path through which the laser is directed and KRS-5 or potassium chloride (KCl) windows on the short path for collecting the infrared spectra of reactants and products. The optical pathlength of the long path is 10.5 cm while the short optical pathlength is 5 cm.

The infrared spectra are recorded on a Bomem DA3.002 interferometer equipped with a vacuum bench and having a deuterated TGS detector and a KBr beamsplitter. The effective resolution is 1 cm$^{-1}$ and 32 scans are taken for each sample and reference. A medium apodization function is used.

The initial sample pressure are measured using an MKS Baratron electronic manometer, consisting of a type 222B transducer and a type PDR-5B power supply/digital readout. Pressures of the $NO_2$ reactant range from about 20 to about 30 torr while the hydrocarbon reactant pressures range from about 200 to about 500 torr.

A Coherent Radiation model 41 CW, $CO_2$ tunable laser provides the energy to drive the reactions, and is operated in a single mode at various selected wavelengths for maximum absorption and powers in the range from about 75 to about 82 W/cm$^2$. The wavelength is verified using an Optical Engineering $CO_2$ spectrum analyzer. The powers are measured by a Coherent Radiation Model 213 water-cooled power meter.

DESCRIPTION OF THE PREFERRED EMBODIMENTS

Laser-induced chemistry is effective in promoting the reaction between a hydrocarbon and $NO_2$ and results in an efficient and a selective procedure. A continuous wave (CW), carbon dioxide ($CO_2$) laser is employed to drive the nitration of several hydrocarbons by nitrogen dioxide ($NO_2$).

The CW, $CO_2$ laser is set to a frequency resonant with a vibrational frequency of the hydrocarbon reactant. If necessary, a sensitizer such as sulfur hexafluoride can be used. Other excitation sources such as a HF/DF laser or an excimer laser can provide access to other regions of the spectrum. With special attention to the absorption spectra of the hydrocarbon reactants, excitation conditions of the tunable $CO_2$ laser can be selected to yield specific desired products at higher yields with minimized product decomposition after product formation.

Figure 1:
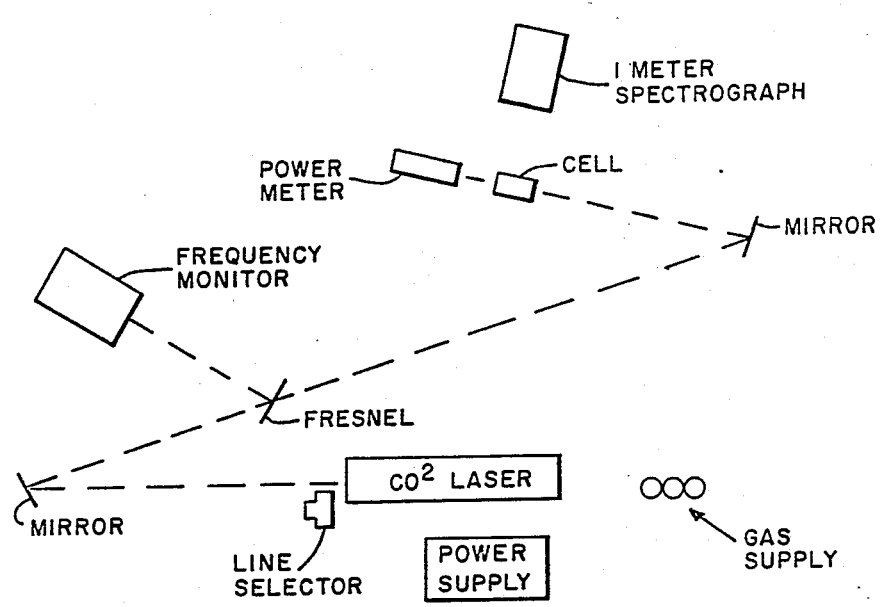
FIG. 1 depicts a typical setup for infrared induced experiments.

Refer to FIG. 1 of the drawing for a typical setup for laser-induced chemistry synthesis. For correlation of the conditions disclosed in detail below under Experimental, a separate list of the Figures of the Drawings depicting drawing number, reactants and conditions for irradiations to obtain the various infrared spectra shown in FIGS. 2-9 of the drawing is shown. Experimental conditions shown on this list relate particularly to the laser-induced reactions between nitrogen dioxide, $NO_2$, and propane, n-butane, and n-pentane to produce nitration products in accordance with the method of this invention.

LIST OF FIGS. 2-9 OF DRAWING WITH SUPPORTING DATA THEREOF

Figure 2:
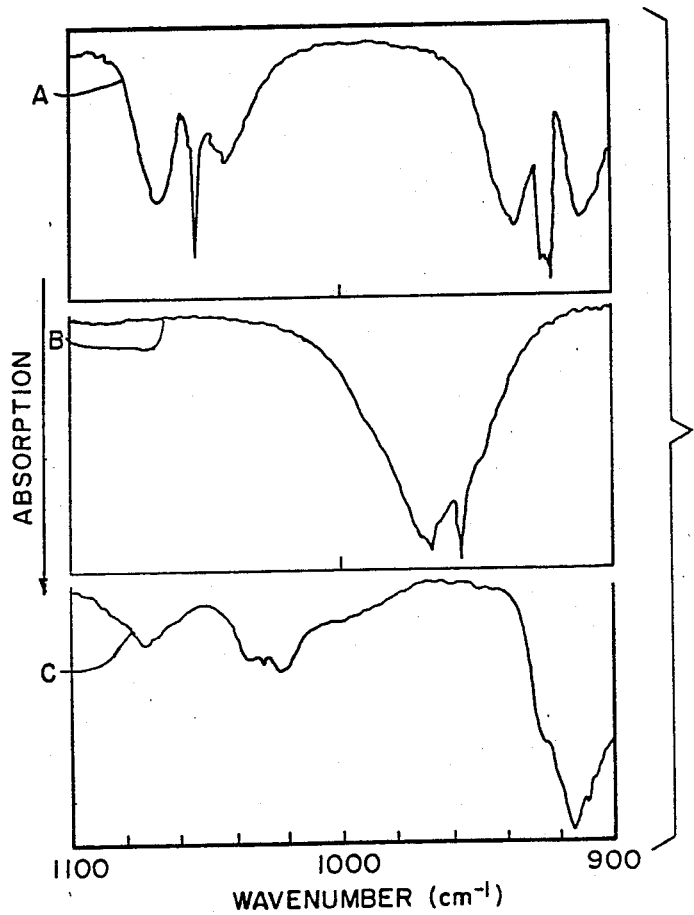
FIG. 2 depicts gas phase mid-infrared spectra: curves A, B and C in the 1100-900 (cm$^{-1}$) region for propane, n-butane, and n-pentane at 200 torr pressure, respectively.
Figure 3:
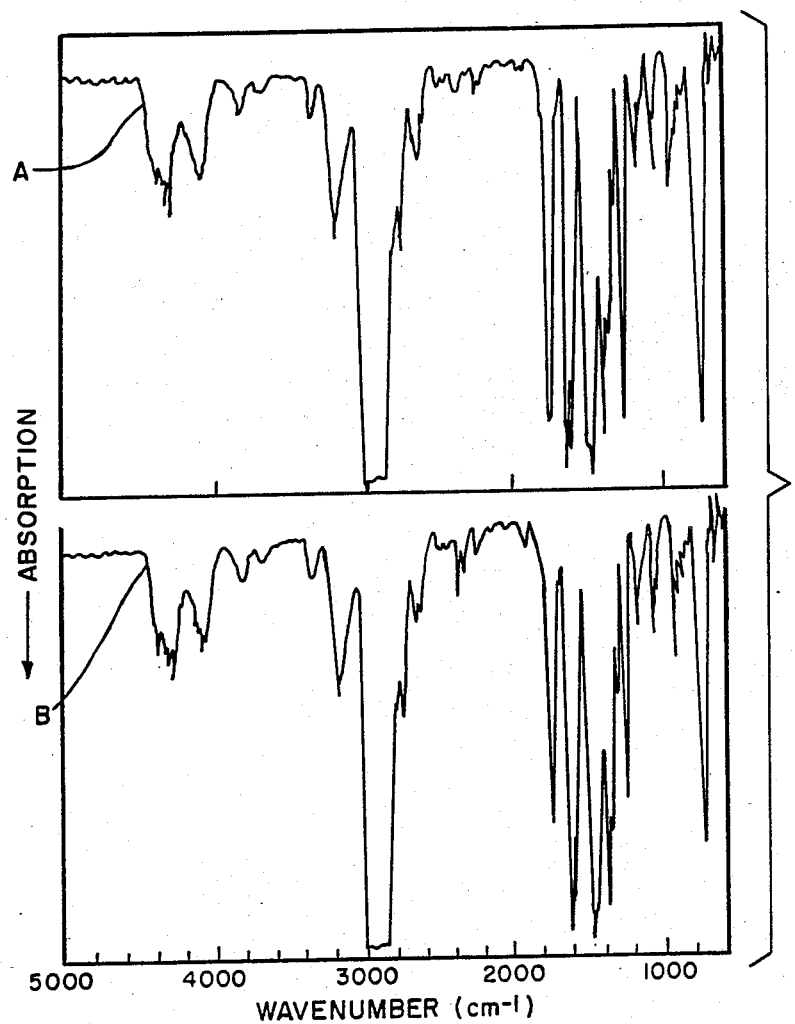
FIG. 3 depicts gas phase mid-infrared spectra: curve A of propane/$NO_2$ mixtures before irradiation and curve B for the products resulting from laser excitation.

FIG. 2. Gas phase mid-infrared spectra in the 1100-900 cm$^{-1}$ region:
  A. Propane, 200 torr
  B. n-butane, 200 torr
  C. n-pentane, 200 torr FIG. 3 Gas phase mid-infrared spectra of propane/$NO_2$ mixtures before irradiation and the products resulting from laser excitation:
  A. Spectra of 470 torr propane and 30 torr $NO_2$
  B. Spectra of products after $CO_2$ laser excitation of the mixture in A using the following conditions P(40) of (00°1-10° 0), 924.9749 cm$^{-1}$ 60 sec; and 82 W/cm$^2$.

Figure 4:
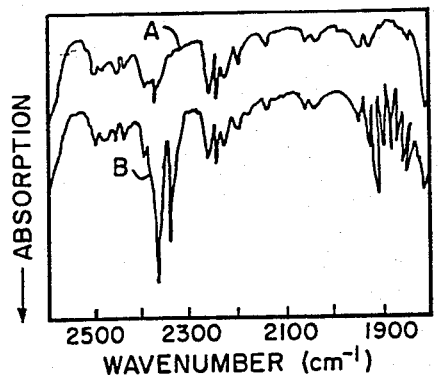
FIGS. 4, 5 and 6 are gas phase infrared spectra of hydrocarbon/$NO_2$ mixtures (curve A) and the products (curve B) resulting from laser excitation for propane, n-butane, and n-pentane, respectively.

FIG. 4 Gas phase infrared spectra of hydrocarbon/$NO_2$ mixtures and the products resulting from laser excitation:
  A. Spectra of propane 470 torr, and $NO_2$, 30 torr.
  B. Spectra of products formed by $CO_2$ laser excitation of the mixture described in A under the following conditions: P(40) of (00°1-10°0), 924.9749 cm$^{-1}$; 60 sec; and 82 W/cm$^2$.

Figure 5:
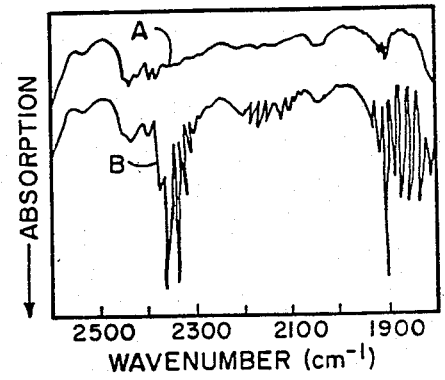

FIG. 5. Gas phase infrared spectra of hydrocarbon/$NO_2$ mixtures and the products resulting from laser excitation:
  A. Spectra of n-butane, 220 torr, and $NO_2$, 20 torr.
  B. Spectra of product formed by $CO_2$ laser excitation of the mixture described in A under the following conditions: P(6) of (00°1-10°0), 956.1857 cm$^{-1}$; 30 sec; and 75 W/cm$^2$.

Figure 6:
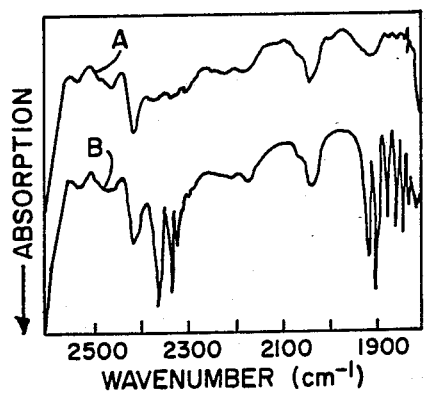

FIG. 6 Gas phase infrared spectra of hydrocarbon/$NO_2$ mixtures and the products resulting from laser excitation:
  A. Spectra of n-pentane, 200 torr, and $NO_2$, 20 torr.
  B. Spectra of products formed by $CO_2$ laser excitation of the mixture described in A under the following conditions: P(40) of (00°1-10°0), 924.9749 cm$^{-1}$; 30 sec; and 75 W/cm$^2$.

Figure 7:
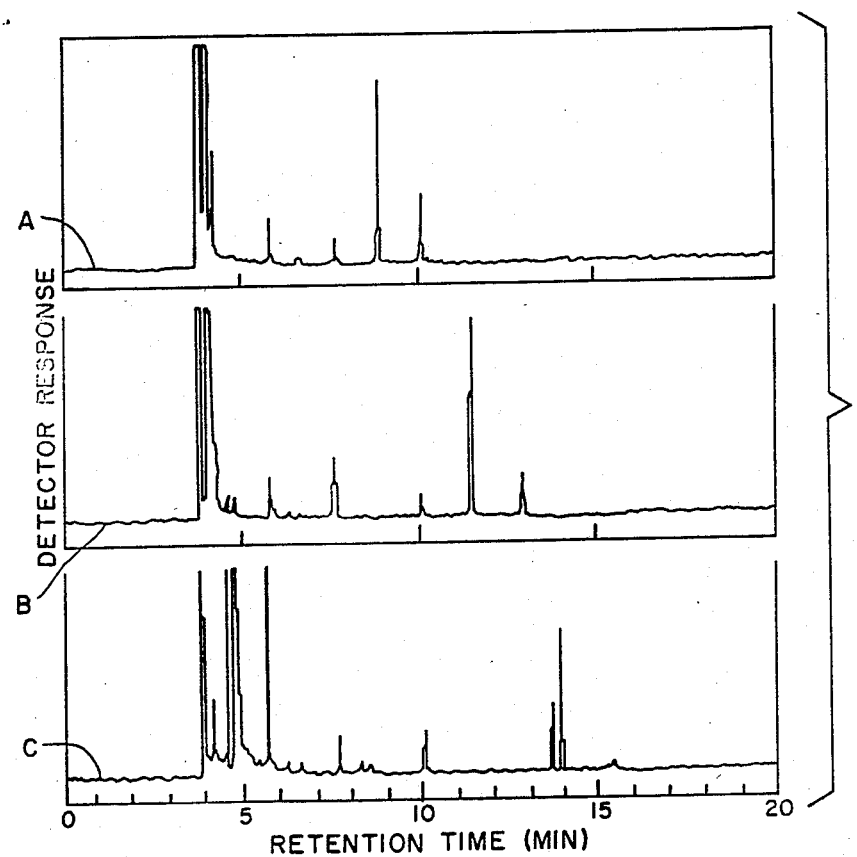
FIG. 7 depicts gas chromatograms: Curves A, B and C depicting detector response (or abundance) on ordinate scale and retention time in minutes on abscissa scale for the products produced by the $CO_2$ laser excitation of $NO_2$ and the hydrocarbons propane, n-butane, and n-pentane, respectively.

FIG. 7 Gas chromatograms from the analysis of product mixes produced by the $CO_2$ laser excitation of hydrocarbon/$NO_2$ mixtures under the following conditions:
  A. Propane, 550 torr, $NO_2$, 30 torr; P(40) of 00°1-10°0), 924.9749 cm$^{-1}$; 60 sec; and 82 W/cm$^2$.
  B. n-butane, 220 torr, $NO_2$, 20 torr: P(40) of (00°1-10°0), 956.1857 cm$^{-1}$, 30 sec; and 75 W/cm$^2$.
  C. n-pentane, 200 torr, $NO_2$, 20 torr: P(40) of 00°1-10°0), 924.9749 cm$^{-1}$; 30 sec; and 75 W/cm$^2$.

Figure 8:
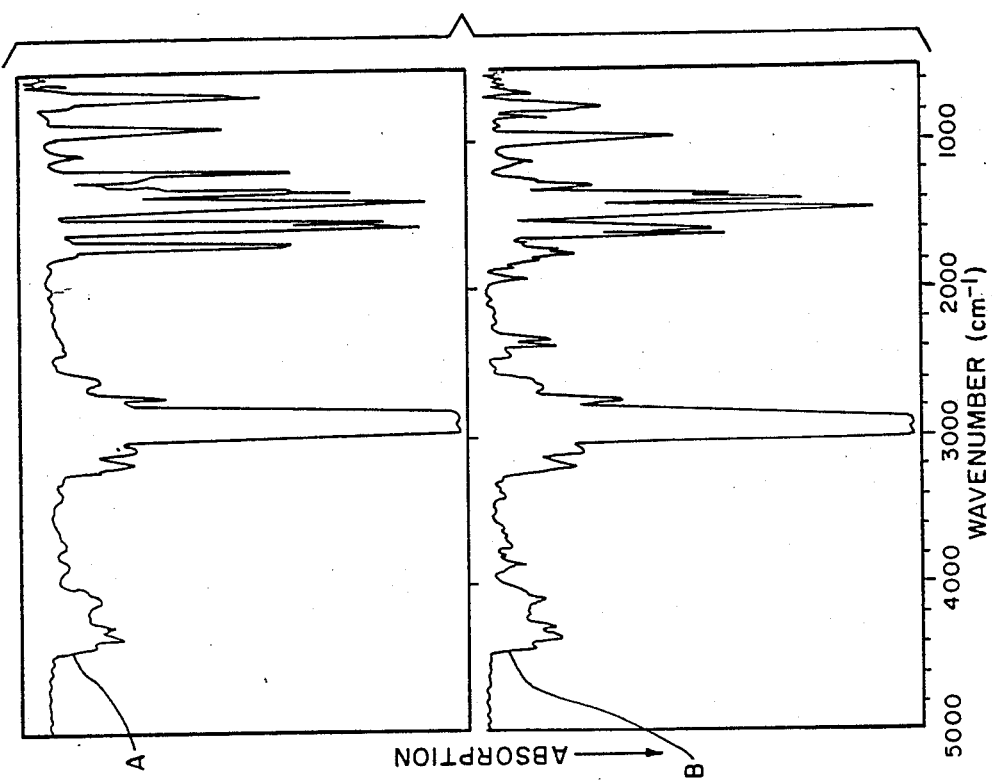
FIG. 8 depicts gas phase mid-infrared spectra: Curve A of butane/$NO_2$ mixtures before excitation and Curve B, products resulting from the $CO_2$ laser excitation of this mixture.

FIG. 8 Gas phase mid-infrared spectra of butane/$NO_2$ mixtures before excitation and products resulting from the $CO_2$ laser excitation of this mixture:

A. Spectra of n-butane, 220 torr, and $NO_2$, 20 torr.

B. Spectra of products formed from the $CO_2$ laser excitation of the mixture in A under the following conditions: P(6) of (00°1–10°0), 956.1857 cm$^{-1}$; 30 sec; and 75 W/cm$^2$.

Figure 9:
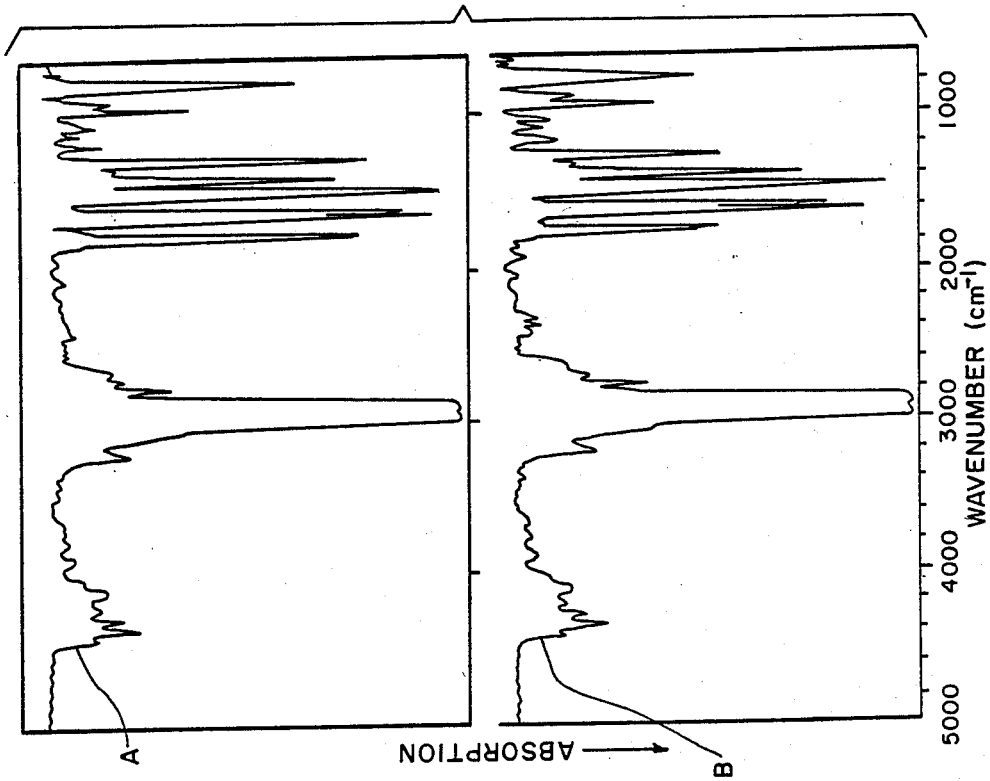
FIG. 9 depicts gas phase mid-infrared spectra Curve A of pentane/$NO_2$ mixtures before excitation and Curve B, the products formed by the $CO_2$ laser excitation of this mixture.

FIG. 9 Gas phase mid-infrared spectra of pentane/$NO_2$ mixtures before excitation and the products formed by the $CO_2$ laser excitation of this mixture:

A. Spectra of n-pentane, 220 torr, and $NO_2$, 200 torr.

B. Spectra of products formed by the $CO_2$ laser excitation of the mixture in A under the following conditions: P(40) of (00°1–10°0), 924.9749 cm$^{-1}$; 30 sec; and 75 W/cm$^2$.

EXPERIMENTAL

Samples of propane, n-butane, n-pentane, nitromethane, nitroethane, 1-nitropropane, 2-nitropropane, 2-methyl-2-nitropropane, 1-nitrobutane, 1-nitropentane, and nitrogen dioxide were obtained from Aldrich Chemical Company, Milwaukee, Wis. The samples were of 98% or greater stated purity except for 2-nitropropane which was 94% stated purity. The purity of the samples was monitored using gas chromatography-mass spectroscopy (GC-MS) and the infrared spectra were compared to published spectra where literature spectra were available (4–8). No further purification of these compounds was undertaken with the exception of nitrogen dioxide which was purified by trap-to-trap separation at −78.5° C. All compounds were degassed at −196.8° C.

Reactants are transferred under vacuum to a stainless steel reaction cell incorporating zinc selenide windows for the laser path and zinc selenide or other windows mounted perpendicular to the laser path in order to record the infrared spectra of the reactants and products. Further analysis of the product is accomplished by gas chromatography/mass spectroscopy (GC/MS).

The laser-induced reaction of the hydrocarbons with $NO_2$ employed an infrared laser, the Coherent Radiation Model 41, in a typical experimental setup as shown in FIG. 1. End product analysis is accomplished using a Hewlett Packard (HP) 5890 interfaced to a HP 5970 series mass selective detector. In this system, unknowns are identified by the comparison of gas chromatographic retention times and mass spectra of the same for knowns. Analysis is assisted by using the National Bureau of Standards (NBS) library of known compounds for comparison. As in other types of chromatography different components move through the bed of packing at different rates and so appear one after another at the effluent end, where they are detected and measured by thermal conductivity changes, density differences, or various types of ionization detectors.

Mixtures of n-butane and $NO_2$ are irradiated by a $CO_2$ laser operating on lines resonant with vibrational bands of butane. Both the P(6) and P(18) lines of the (00°1–(10°0) band at 956.1857 and 945.9810 cm$^{-1}$, respectively, were utilized, with the P(6) line resulting in slightly higher yields of nitrated products.

As shown below in Table 1, the primary product of the nitration of n-butane by $NO_2$ under the conditions employed is identified as 2-nitrobutane, based on its mass spectrum and retention time relative to 1-nitro-2-methylpropane and 1-nitrobutane. If similar instrument response of 1-nitrobutane and the instrument response to the product of nitration are compared, then 15% a conservative estimate of the yield of the primary product based on initial $NO_2$ pressure. For this yield, initial pressures were 180 torr for butane and 20 torr for $NO_2$. The laser was operating on the P(6) line at a power of 75 W and for a duration of 30 seconds. However, the vapor pressure of 2-nitrobutane is expected to be quite a low at room temperature, therefore the yield of 2-nitrobutane may be higher than that estimated. Modifications of the experimental design can be made to provide for a more reliable estimation of the yield under a variety of laser prowers, irradiation times, and reactant compositions. Where there was a question of product identity, a note, "not identified," is listed as a footnote for Table 1 and subsequent Tables presented hereinbelow.

TABLE 1

Summary of GC-MS Data from the Analysis of the Products of the Laser-Induced Nitration of Butane with $NO_2$.

| Retention Time | Area | Area % | Ratio % | Compounds Identified | Amount Torr* |
|---|---|---|---|---|---|
| 3.916 | 11882909 | 3.14 | 3.44 | More than 1 component | — |
| 4.027 | 4948455 | 1.31 | 1.44 | Butane Impurity | — |
| 4.095 | 504639 | 0.13 | 0.15 | ** | — |
| 4.147 | 4432765 | 1.17 | 1.28 | ** | — |
| 4.242 | 3.459E8 | 91.27 | 100.00 | Butane | — |
| 4.621 | 861449 | 0.23 | 0.25 | ** | — |
| 4.835 | 666027 | 0.18 | 0.19 | ** | — |
| 5.836 | 892597 | 0.24 | 0.26 | Nitromethane | 1.1 |
| 6.605 | 178691 | 0.05 | 0.05 | ** | — |
| 7.681 | 1782231 | 0.47 | 0.52 | Nitroethane | 1.4 |
| 10.10 | 556120 | 0.15 | 0.16 | 1-nitropropane | 0.5 |
| 11.49 | 4668849 | 1.23 | 1.35 | 2-nitrobutane | 4.0 |
| 12.93 | 1032901 | 0.27 | 0.30 | 1-nitrobutane | 0.9 |

*Conditions employed in this reaction were: n-butane pressure, 220 torr; $NO_2$ pressure, 20 torr; laser line, P(6) of (00°1–10°0); laser power, 75 W/cm$^2$; irradiation time, 30 sec. The estimated amounts of nitroparaffin products, except 2-nitrobutane, are based on calibration of the instrument response when known pressures of these compounds were placed in the reaction cell and injected through the gas sampling loop. The pressure of 2-nitrobutane produced is estimated based on the calibration of 1-nitrobutane.
**Not Identified Small amounts of other products are formed in the reaction as well. These products appear to be primarily other mononitrated hydrocarbons of $C_4$ chain length and below.

A $CO_2$ laser is used to drive the reaction of propane with $NO_2$. The $CO_2$ laser operated on the P(40) line of the (00°0) band at a power of 100 W for a period of 60 seconds in order to cause a reaction. The primary product is 2-nitropropane, with other nitrated products formed in smaller amounts (see Table 2). A yield of 9% 2-nitropropane is estimated for this reaction. Higher yields are expected when the conditions are optimized.

TABLE 2
Summary of GC-MS Data from the Analysis of the Products of the Laser-Inducted Nitration of Propane with NO$_2$.

| Retention Time | Area | Area % | Ratio % | Compounds Identified | Amount Torr* |
|---|---|---|---|---|---|
| 3.921 | 9145594 | 2.03 | 2.12 | More than 1 component | — |
| 4.018 | 4.310E8 | 95.78 | 100.00 | propane | — |
| 4.227 | 3090683 | 0.69 | 0.72 | butane (not conclusive) | — |
| 4.774 | 212605 | 0.05 | 0.05 | ** | — |
| 4.831 | 334010 | 0.07 | 0.08 | ** | — |
| 5.372 | 314391 | 0.07 | 0.07 | ** | — |
| 5.840 | 781757 | 0.17 | 0.18 | nitromethane | 1.5 |
| 6.550 | 314391 | 0.07 | 0.07 | ** | — |
| 7.668 | 501706 | 0.11 | 0.12 | nitroethane | 0.8 |
| 8.922 | 3268045 | 0.73 | 0.76 | 2-nitropropane | 1.7 |
| 10.10 | 1040723 | 0.23 | 0.24 | 1-nitropropane | 0.7 |

*Conditions employed in this reaction were: propane pressure, 470 torr; NO$_2$ pressure, 30 torr; laser line, P(40) of (00°1–10°0); laser power, 82 W/cm$^2$; irradiation time, 60 sec. The estimated amounts of nitroparaffin products are based on calibration of the instrument response when known pressures of these components were placed in the reaction cell and injected through the gas sampling loop.
**Not Identified

TABLE 3
Summary of GC-MS Data from the Analysis of the Products of the Laser-Induced Nitration of n-Pentane with NO$_2$.

| Retention Time | Area | Area % | Ratio % | Compounds Identified | Amount Torr* |
|---|---|---|---|---|---|
| 3.905 | 5002700 | 1.25 | 1.34 | More than 1 component | — |
| 4.010 | 1404895 | 0.35 | 0.38 | Pentane impurity** | — |
| 4.075 | 408476 | 0.10 | 0.11 | Pentane impurity** | — |
| 4.129 | 491759 | 0.12 | 0.13 | Pentane impurity** | — |
| 4.203 | 1288258 | 0.33 | 0.34 | Pentane impurity** | — |
| 4.605 | 3178313 | 0.80 | 0.85 | Pentane impurity** | — |
| 4.792 | 3.7409E8 | 94.40 | 100.00 | Pentane | — |
| 4.887 | 1220945 | 0.31 | 0.33 | ** | — |
| 5.134 | 279689 | 0.07 | 0.07 | ** | — |
| 5.181 | 382545 | 0.10 | 0.10 | ** | — |
| 5.684 | 3496246 | 0.88 | 0.93 | Pentane impurity | — |
| 7.663 | 528792 | 0.13 | 0.14 | Nitroethane | 0.8 |
| 8.274 | 226095 | 0.06 | 0.06 | ** | — |
| 10.08 | 587932 | 0.15 | 0.16 | 1-nitropropane | 0.5 |
| 13.69 | 993117 | 0.25 | 0.27 | 3-nitropentane | 0.9 |
| 13.98 | 2070157 | 0.52 | 0.55 | 2-nitropentane | 1.9 |
| 15.49 | 248895 | 0.06 | 0.07 | 1-nitropentane | 0.6 |

*Conditions employed in this reaction were: n-pentane pressure, 220 torr; NO$_2$ pressure, 20 torr; laser line, P(40) of (00°1–10°0); laser power, 75 W/cm$^2$; irradiation time, 30 sec. The estimated amounts of nitroparaffin products, except 2-nitropentane and 3-nitropentane, are based on calibration of the instrument response when known pressures of these components were placed in the reaction cell and injected through the gas sampling loop. The pressures of 2-nitropentane and 3-nitropentane produced is estimated based on the calibration of 1-nitropentane.
**Not Identified The laser-induced nitration of pentane with NO$_2$ is accomplished using the P(40) line of the (00°1–10°0) transition of the CO$_2$ laser. The major nitrated product is 2-nitropentane, and a yield of about 9% is estimated for this nitroalkane. About half as much of a product identified as 3-nitropentane is formed as well. Other products include 1-nitropentane, 1-nitropropane, and 1-nitroethane (see Table 3 above).

Vapor phase nitration of hydrocarbons with NO$_2$ is known to require temperatures on the order of 200°–400° C. for reaction to occur (See R. E. Kirk and D. F. Othmer, "Encyclopedia of Chemical Technology," 2nd Edition, V13, New York, Wiley, 784 (1967).)

The higher one goes in temperature the greater the number of side products from oxidation and bond breaking. In our analysis the only oxidized products identified so far, are the oxides of carbon, materials which are easily pumped away. As Table 4 shows, 62% of the butane nitration products are long chain nitrobutanes. This indicates a minimum of C-C bond breakage. The photonitrations with NO$_2$ have been reported by F. E. Blacet, et, al, J. Amer. Chem. Soc., 84, 4011; however, irradiation times require hours, even months to obtain appreciable products.

TABLE 4
Relative Proportion of Nitrated Products
Relative Amounts of Nitroalkane Products*

| Reacting Alkane | Total Yields | NM | NE | 1-NPr | 2-NPr | 1-NB | 2-NB | 1-NP | 2-NP | 3-NP |
|---|---|---|---|---|---|---|---|---|---|---|
| Propane | 15% | 32 | 17 | 15 | 36 | | | | | |
| n-butane | 40% | 14 | 18 | 6 | | 11 | 51 | | | |

TABLE 4-continued

| | | Relative Proportion of Nitrated Products Relative Amounts of Nitroalkane Products* | | | | | | | | |
|---|---|---|---|---|---|---|---|---|---|---|
| Reacting Alkane | Total Yields | NM | NE | 1-NPr | 2-NPr | 1-NB | 2-NB | 1-NP | 2-NP | 3-NP |
| n-pentane | 23% | 17 | 11 | | | | | 13 | 40 | 19 |

*Abbreviations used:
NM = nitromethane.
NE = nitroethane.
1-NPr = 1-nitropropane.
2-NPr = 2 nitropropane.
1-NB = 1-nitrobutane.
2-NB = 2-nitrobutane.
1-NP = 1-nitropentane.
2-NP = 2-nitropentane.
3-NP = 3 nitropentane.
These percentages represent a distribution of nitrated products within the total yield.

Table 5 below shows that laser-induced nitration products for the reactants propane, butane, and pentane are produced in higher yields in applicants' method as compared with thermally-induced nitrations. The laser-induced nitration products are more free from decomposition products than the thermally induced nitrations which render the laser-induced nitration products superior for propellant use.

TABLE 5

Comparison of Nitroalkane Products from Laser-Induced Nitrations to Thermally-Induced* Nitrations.

| Hydrocarbon | Product | Thermal** Mole % | Laser-Induced |
|---|---|---|---|
| Propane | Nitromethane | 22.0 (32.3) | 32 |
| | Nitroethane | 16.6 (24.2) | 17 |
| | 1-nitropropane | 13.2 (24.2) | 15 |
| | 2-nitropropane | 48.2 (19.3) | 36 |
| Butane | Nitromethane | 10.5 | 14 |
| | Nitroethane | 15.8 | 18 |
| | 1-nitropropane | 5.3 | 6 |
| | 1-nitrobutane | 24.2 | 11 |
| | 2-nitrobutane | 44.2 | 51 |
| Pentane | Nitromethane | 2.3 | ***Not determined |
| | Nitroethane | 10.9 | 17 |
| | 1-nitropropane | 16.7 | 11 |
| | 1-nitrobutane | 12.8 | 0 |
| | 1-nitropentane | 18.9 | 13 |
| | 2-nitropentane | 18.2 | 40 |
| | 3-nitropentane | 20.2 | 19 |

Ref. *H. B. Hass and H. Shechter, Ind. Eng. Chem. 39,817 (1947) and references therein.
**The temperatures used in the thermally-induced nitrations (Ref. * above), were as follows: Propane: 505–10° C. for first set of numbers; 790–50° C. for numbers in parentheses. Butane: 420° C. Pentane: 400° C.
***An impurity of the pentane sample obscured any chromatographic peak from nitromethane.

The projections from this invention and the initial experimentation into the selective nitrations of hydrocarbons are very promising.

Experimental conditions, such as the ratio of reactants, total pressure of reactants, laser power, and duration of irradiation can be optimized. Other laser sources can be expected, after optimization, to obtain maximum yields. Thus laser-induced selective nitrations appear to have the potential of attaining yields as high as the thermal processes with few side products.

We claim:

1. A method for the laser-induced nitrations of hydrocarbons to selectively nitrate said hydrocarbons toward specific nitrated hydrocarbon end products required for propellants with the chemical composition necessary to burn exactly with high energy production without producing undesirable smoke as a result of side products formed during said selectively nitration including a minimum of decomposition products formed as a result of low absorption threshold by said nitrated end products for said wavelength employed to selectively nitrate said hydrocarbons, said method comprising completing the laser-induced chemical reaction between a first reactant selected from the hydrocarbons consisting of propane, n-butane, and n-pentane and a second reactant of a nitrating compound selected from nitrogen dioxide and nitric acid to form said nitrated hydrocarbons in accordance with completing the following steps and procedures which comprise:

(i) providing a stainless steel reaction cell adapted for use with vacuum line techniques and equipped with O-ring seals for securing ZnSe windows onto said reaction cell for transmitting laser radiation and for securing potassium chloride windows onto said reaction cell to achieve monitoring of said laser-induced chemical reaction including the reaction products formed;

(ii) metering said first reactant of said hydrocarbon and said second reactant of said nitrating compound into said reaction cell to form a reaction mixture of said hydrocarbons in the range from about 200 to about 500 torr and of said nitrogen dioxide or nitric acid in the range from about 20 to about 30 torr;

(iii) irradiating said reaction mixture with infrared laser radiation in the range of 10.4 or 9.4 micrometers as provided by a continuous-wave $CO_2$ laser operating in a predetermined single line operation with an output power from about 75 watts per centimeter square ($W/cm^2$) to about 82 watts per centimeter square ($W/cm^2$) to form said nitrated hydrocarbon end products; and, (iv) recovering said nitrated hydrocarbon end products.

2. The method of claim 1 wherein said first reactant is propane, said second reactant of said nitrating compound is nitrogen dioxide, said reaction mixture comprises said propane of about 470 torr and said nitrogen dioxide of about 30 torr, and wherein laser excitation of said mixture is achieved by said predetermined single line operation at P (40) of (00°1–10°0) for about 60 seconds at 924.9749 $cm^{-1}$ with said output power of about 82 $W/cm^2$ to form said nitrated hydrocarbons in about 15 percent yield comprising nitromethane, nitroethane, 1-nitropropane, and 2-nitropropane in relative ratio amounts of 32:17:15: and 36 respectively.

3. The method of claim 1 wherein said first reactant is n-butane, said second reactant of said nitrating compound is nitrogen dioxide, said reaction mixture comprises said propane of about 220 torr and said nitrogen dioxide of about 20 torr, and wherein laser excitation of said mixture is achieved by said predetermined single line operation at P (18) of (00°1–10°0) for about 60 seconds at 945.9810 cm$^{-1}$ with said output power of about 75 W/cm$^2$ to form said nitrated hydrocarbons.

4. The method of claim 1 wherein said first reactant is n-butane, said second reactant of said nitrating compound is nitrogen dioxide, said reaction mixture comprises said propane of about 220 torr and said nitrogen dioxide of about 20 torr, and wherein laser excitation of said mixture is achieved by said predetermined single line operation at P(6) of (00°1–10°0) for about 30 seconds at 956.1857 cm$^{-1}$ with said nitrated hydrocarbons in about 40 percent yield comprising nitromethane, nitroethane, 1-nitropropane, 1-nitrobutane, and 2-nitrobutane in relative ratio amounts of 14:18:6:11: and 51, respectively.

5. The method of claim 1 wherein said reactant is n-pentane, said second reactant of said nitrating compound is nitrogen dioxide, said reaction mixture comprises said propane of about 220 torr and said nitrogen dioxide of about 20 torr, and wherein laser excitation of said mixture is achieved by said predetermined single line operation at P(40) of (00°1–10°0) for about 30 seconds at 924.9749 cm$^{-1}$ with said output power of about 75 W/cm$^2$ to form said nitrated hydrocarbons in about 23 percent yield comprising nitroethane, 1-nitropropane, 2-nitropropane, and 3-nitropane in relative ratio amounts of 19:11:13:40: and 19, respectively.

* * * * *